United States Patent
Asami et al.

(10) Patent No.: US 6,649,568 B2
(45) Date of Patent: Nov. 18, 2003

(54) BRASSINOSTEROID BIOSYNTHESIS INHIBITOR

(75) Inventors: Tadao Asami, Tokyo (JP); Shigeo Yoshida, Tokyo (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 10/204,435

(22) PCT Filed: Mar. 2, 2001

(86) PCT No.: PCT/JP01/01605
§ 371 (c)(1),
(2), (4) Date: Nov. 26, 2002

(87) PCT Pub. No.: WO01/64657
PCT Pub. Date: Sep. 7, 2001

(65) Prior Publication Data
US 2003/0166468 A1 Sep. 4, 2003

(30) Foreign Application Priority Data
Mar. 2, 2000 (JP) ........................ 2000-057565

(51) Int. Cl.⁷ ...................... A01N 43/653; C07D 249/08
(52) U.S. Cl. ...................... 504/180; 504/272; 504/274; 548/268.2
(58) Field of Search ........................ 548/268.2; 504/274, 504/180

(56) References Cited

U.S. PATENT DOCUMENTS

| | | | |
|---|---|---|---|
| 4,923,503 A | 5/1990 | Schulz et al. | |
| 4,969,950 A | 11/1990 | Lauer et al. | |
| 4,992,458 A | 2/1991 | Riebli et al. | |
| 6,388,089 B1 * | 5/2002 | Yoshida et al. | 548/262.2 |

FOREIGN PATENT DOCUMENTS

| | | |
|---|---|---|
| JP | 2000-53657 | 2/2000 |

OTHER PUBLICATIONS

English Language Abstract of JP 2000–53657.
Takao Yokota, "The Structure, Biosynthesis and Function of Brassinosteroids", *Trends in Plant Science*, vol. 2, No. 4, pp. 137–143 (1997).
N. Bhushan Mandava, "Plant Growth–Promoting Brassinosteroids", *Ann. Rev. Plant Physiol. Plant Mol. Biol.*, vol. 39, pp. 23–52 (1988).
Carl Schlagnhaufer et al., "Evidence that Brassinosteroids Stimulates Auxin–Induced Ethylene Synthesis in Mung Bean Hypocotyls Between S–Adenosylmethionine and 1–Aminocyclopropane–1–Carboxylic Acid", *Physiol. Plant*, vol. 61, pp. 555–558 (1984).
Toshisuke Iwasaki et al., "Brassinosteroids Act as Regulators of Tracheary–Element Differentiation in Isolated Zinnia Mesophyll Cells", *Plant Cell Physiol.*, vol. 32, No. 7, pp. 1007–1014 (1991).

Ryo Yamamoto et al., "Brassinosteroids Induces Entry into the Final Stage of Tracheary Element Differentiation in Cultured Zinnia Cells", *Plant Cell Physiol.*, vol. 38, No. 8, pp. 980–983 (1997).
Ricardo Azpiroz et al., "An Arabidopsis Brassinosteroid–Dependent Mutant Is Blocked in Cell Elongation", *The Plant Cell*, vol. 10, pp. 219–230 (1998).
Steven D. Clouse, "Molecular Genetic Studies Confirm the Role of Brassinosteroids in Plant Growth and Devolopment", *The Plant Journal*, vol. 10, No. 1, pp. 1–8 (1996).
Shozo Fujioka et al., "Biosynthesis and Metabolism Brassinosteroids", *Phyiologia Plantarum*, vol. 100, pp. 710–715 (1997).
Kenneth A. Feldman et al., "A Dwarf Mutant of Arabidopsis Generated by T–DNA Insertion Mutagenesis", *Science*, vol. 243, pp. 1351–1354 (1989).
Taku Takahashi et al., "The Diminuto Gene of Arabidopsis in Involved in Regulating Cell Elongation", *Genes & Development*, vol. 9, pp. 97–107 (1995).
Annette Kauschmannn et al.,"Genetic Evidence for an Essential Role of Brassinosteroids in Plant Development", *The Plant Journa*, vol. 9, No. 5, pp. 701–713 (1996).
Miklos Szekeres et al., "Brassinosteroids Rescue the Deficiency of CYP90, A Cytochrome P450, Controlling Cell Elongation and De–Etiolation in Arabidopsis", *Cell*, vol. 85, p. 171–182 (1996).
Jianming Ll et al., "A Role for Brassinosteroids in Light–Dependent Development of Arabidopsis", *Science*, vol. 272, pp. 398–401, (1996).
Shozo Fijioka et al., "the Arabidopsis Deetiolated2 Mutant is Blocked Early in Brassinosteroid Biosynthesis", *The Plant Cell*, vol. 9, pp. 1951–1962 (1997).
Takahito Nomura et al., "Blockage of Brassinosteroid Biosynthesis and Sensitivity Causes Dqarfism in Garden Peas", *Plant Physiol.*, vol. 113, pp. 31–37 (1997).
T. Yokota et al., "Chapter 33: Inconsistency Between Growth and Endogenous Levels of Gibberellins, Brassinosteroids, and Sterols in *Pisum Sativum* Treated with Uniconazole Antipodes", *Gibberellin*, Springer Verlag, New York, pp. 339–349 (1991).

* cited by examiner

*Primary Examiner*—Robert W. Ramsuer
(74) *Attorney, Agent, or Firm*—Greenblum & Bernstein, P.L.C.

(57) ABSTRACT

Compounds represented by the following formula (I):

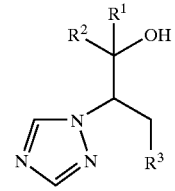

wherein $R^1$ represents a lower alkenyl group or a phenyl group which may be substituted, $R^2$ and $R^3$ independently represent a phenyl group which may be substituted or salts thereof, and a plant growth regulator which comprises said compound or a salt thereof as an active ingredient.

9 Claims, 2 Drawing Sheets

BRASSINOSTEROID BIOSYNTHESIS INHIBITOR

TECHNICAL FIELD

The present invention relates to a compound having inhibitory action against the brassinosteroid biosynthesis and a plant growth regulator comprising said compound.

BACKGROUND ART

Brassinosteroids have recently recognized as a new class of plant hormones through the combination of molecular genetics and researches on biosyntheses (Yokota, Trends in Plant Sci., 2, pp.137–143, 1997). Since the chemistry of brassinosteroids was established, biological activities of these homologues have been extensively studied, and their notable actions on plant growth have been revealed, which include elongation of stalks, growth of pollen tubes, inclination of leaves, opening of leaves, suppression of roots, activation of proton pump (Mandava and Annu. Rev. Plant Physiol. Plant Mol. Biol., 39, pp.23–52, 1988), acceleration of ethylene production (Schlagnhaufer et al., Physiol. Plant, 61, pp.555–558, 1984), differentiation of vessel elements (Iwasaki et al., Plant Cell Physiol., 32, pp.1007–1014, 1991; Yamamoto et al., Plant Cell Physiol., 38, pp.980–983, 1997), and cell extension (Azpiroz et al., Plant Cell, 10, pp.219–230, 1998).

Furthermore, mechanisms and regulations of physiological actions of brassinosteroids have been being revealed by variety of studies on their biosynthesis (Clouse, Plant J. 10, pp.1–8, 1996; Fujioka et al., Physiol. Plant, 100, pp.710–715, 1997). At present, 40 or more brassinosteroids have been identified. Most of C28-brassinosteroids are common vegetable sterols, and they are considered to be biosynthesized from campesterol which has the same carbon side chain as that of brassinolide.

Some Arabidopsis mutants which show characteristic dwarfism have been isolated, i.e., dwf1: Feldman et al., Science, 243, pp.1351–1354, 1989; dim: Takahashi et al., Genes Dev., 9, pp.97–107, 1995; cbb1: Kauschmann et al., Plant J., 9, pp.701–703, 1996. Their structural photomorphogenesis and dwarfism (cpd; Szekeres et al., Cell, 85, pp.171–182, 1997) and de-etiolation (det2: Li et al., Science, 272, pp.398–401, 1996; Fujioka et al., Plant Cell, 9, pp.1951–1962, 1997) are known. The mutants have deficiencies in the brassinosteroid biosynthetic pathway. Further, a dwarf mutant of Pisum sativum was recently characterized, and the mutant was reported as a brassinosteroid deficient mutant (Nomura et al., Plant Physiol., 113, pp.31–37, 1997). In these plants, use of brassinolide is known to negate severe dwarfism of the mutants. Although these findings suggest that roles of brassinosteroids are indispensable for growth and development of plants, an effective tool other than the analysis of mutants has been desired to elucidate physiological importance of brassinolide.

As seen in researches of gibberellin action, specific inhibitors against the biosynthesis are generally very effective tools for elucidating physiological functions of endogenous substances. Specific inhibitors for the brassinosteroid biosynthesis are expected to provide a new tool for understanding the functions of brassinosteroids. Uniconazol is a potent plant growth regulator (PGR) which inhibits the oxidation employed by cytochrome P-450 in the steps of the gibberellin biosynthesis from ent-kaurene to ent-kaurenoic acid. Yokota et al. observed slight reduction of the amount of endogenous castasterone as a side effect of that compound (Yokota et al., "Gibberellin", Springer Verlag, New York, pp.339–349, 1991). Although uniconazole inhibits differentiation of vessel elements induced by brassinolide (Iwasaki et al., Plant Cell Physiol., 32, pp.1007–1014, 1991), its inhibitory action against brassinolide is considered to be no more than an incidental action, because uniconazol essentially inhibits the gibberellin biosynthesis.

DISCLOSURE OF THE INVENTION

An object of the present invention is to provide a specific inhibitor against the brassinosteroid biosynthesis. Some mutants which are deficient in enzymes for biosynthesis are known for Arabidopsis, and their morphologic changes are unique to mutants with deficiency in the brassinosteroid biosynthesis. Therefore, the inventors of the present invention conducted intensive search for a compound inducing the morphologic changes unique to the mutants with the brassinosteroid biosynthesis deficiency to find a specific inhibitor against the brassinosteroid biosynthesis. As a result, they found that triazole compounds such as 4-(4-chlorophenyl)-2-phenyl-3-(1,2,4-triazoyl)butan-2-ol had the desired inhibitory action (the specification and claims of Japanese Patent Application No. 10-227939). The inventor further conducted researches, and found that the triazole compounds represented by the following formula (I) had more potent activities. The present invention was achieved on the basis of these findings.

The present invention thus provides a compound represented by the following formula (I):

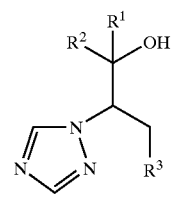

wherein $R^1$ represents a lower alkenyl group or a phenyl group which may be substituted, $R^2$ and $R^3$ independently represent a phenyl group which may be substituted, or a salt thereof. According to a preferred embodiment of the present invention, provided is the aforementioned compound or a salt thereof wherein $R^1$ is vinyl group, allyl group, butenyl group, or phenyl group, and $R^2$ is a phenyl group which may be substituted with a halogen atom, and $R^3$ is p-chlorophenyl group.

From another aspect of the present invention, there are provided an inhibitor against the brassinosteroid biosynthesis which comprises the compound represented by the aforementioned formula (I) or a physiologically acceptable salt thereof. The inhibitor of the present invention can be used as a plant growth regulator for, for example, suppression of plant elongation, suppression of pollen growth, retention of freshness of flowers, anti-stress agents for plants, weeds control, suppression of plant retrogradation, hypertrophism of roots and the like.

According to further aspects of the present invention, there are provided a use of the compound represented by the aforementioned formula (I) or a salt thereof for the inhibitor against the brassinosteroid biosynthesis, a method for inhibiting brassinosteroid biosynthesis which comprises the step of administering the compound of the aforementioned formula (I) or a salt thereof to a plant; and a method for regulating plant growth, which comprises the step of administering the compound of the aforementioned formula (I) or a salt thereof to a plant.

BEST MODE FOR CARRYING OUT THE INVENTION

Figure 1:
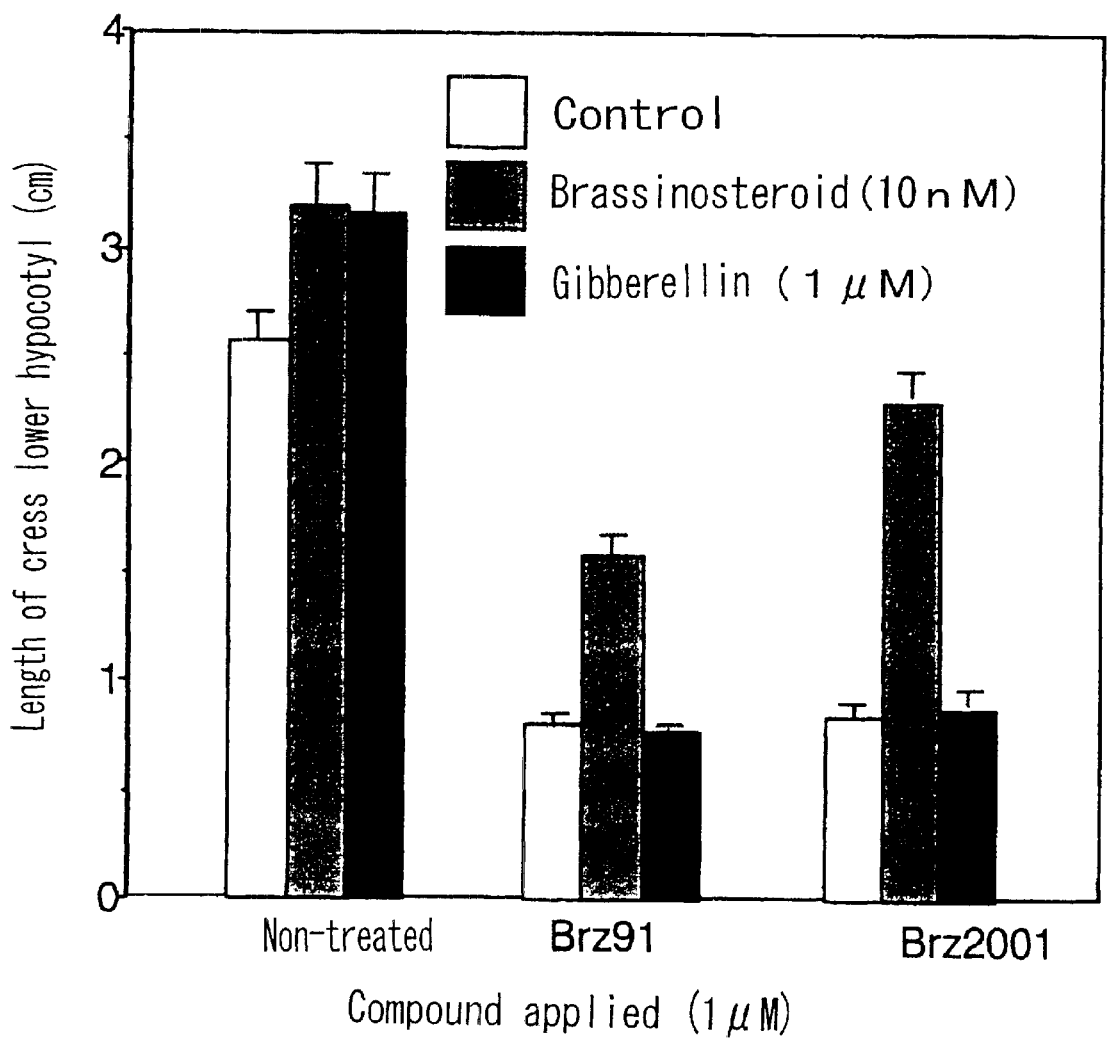
FIG. 1 shows that the compound of the present invention has inhibitory action on elongation of cress lower hypocotyl, and the inhibitory action is suppressed by addition of brassinosteroid, whilst not suppressed by addition of gibberellin.

All disclosures of the specification and claims of Japanese patent application No. 2000-57565 are incorporated in disclosures of the present specification by reference.

In the aforementioned formula (I), $R^1$ represents a lower alkenyl group or a phenyl group which may be substituted. As the lower alkenyl group, a linear or branched alkenyl group having 1 to about 6 carbon atoms can be used. Examples include vinyl group, allyl group, and 2-butenyl group, which are preferred embodiments of the present invention. When the phenyl group represented by $R^2$ or $R^3$ is substituted, types, numbers and substituting positions of substituents are not particularly limited. For example, the phenyl group may have preferably 1 to 3, more preferably 1 or 2 of substituents. Where the phenyl group has 2 or more substituents, they may be the same or different.

Examples of the substituent on the phenyl group include, for example, a halogen atom (any of fluorine atom, chlorine atom, bromine atom and iodine atom), a lower alkyl group (methyl group, ethyl group and the like), a lower cycloalkyl group (cyclopropyl group and the like), a halogenated lower alkyl group (trifluoromethyl group and the like), a lower alkoxy group (methoxy group, ethoxy group and the like), amino group, mono- or dialkylamino group, carboxyl group, an alkoxycarbonyl group (ethoxycarbonyl group and the like), an alkanoyl group (acetyl group and the like), an aroyl group (benzoyl group and the like), an aralkyl group (benzyl group and the like), an aryl group (phenyl group and the like), a heteroaryl group (pyridyl group and the like), heterocyclic group (pyrrolidinyl group and the like), hydroxyl group, nitro group, cyano group and so forth. However, the substituents are not limited to these examples. Among them, a halogen atom, a lower alkyl group, a halogenated lower alkyl group, a lower alkoxy group and the like are preferred. An example of the substituted phenyl group represented by $R^2$ includes 2,4-difuluorophenyl group, and an example of the substituted phenyl group represented by $R^3$ includes 4-chlorophenyl group.

The compounds of the present invention have two asymmetric carbon atoms in the fundamental structure, and may have one or more further asymmetric carbon atoms depending on the type of the substituent. Optically active compounds and diastereoisomers in pure forms based on the asymmetric carbon atoms as well any mixtures of the isomers (for example, mixtures of two or more of diastereoisomers), racemates and so forth fall within the scope of the present invention. Further, the compounds of the present invention may form acid addition salts, and may further form acid addition salts depending on the type of the substituent. The types of the salts are not particularly limited, and examples of the salts include salts with mineral acids such as hydrochloric acid, and sulfuric acid, salts with organic acids such as p-toluenesulfonic acid, methanesulfonic acid, and tartaric acid, metal salts such as sodium salts, potassium salts, and calcium salts, ammonium salts, salts with organic amines such as triethylamine, salts with amino acids such as glycine and so forth.

Specific examples of the compounds of the present invention will be shown in Tables 1 and 2 below. However, the compounds of the present invention are not limited to these examples. In the table, Phenyl represents a phenyl group, and as for substituents X and X, the number added before the substituent indicate a substituting position. For example, a phenyl group wherein X is indicated as 2-Cl, 4-F, and 2,4-diF represents 2-chlorophenyl group, 4-fluorophenyl group, and 2,4-difluorophenyl group, respectively. Other groups are indicated in a similar manner.

TABLE 1

| $R^1$ | X | Y |
|---|---|---|
| —CH=CH$_2$ | H | H |
| —CH=CH$_2$ | H | 4-F |
| —CH=CH$_2$ | H | 4-Cl |
| —CH=CH$_2$ | H | 4-Br |
| —CH=CH$_2$ | H | 4-CF$_3$ |
| —CH=CH$_2$ | 2-F | H |
| —CH=CH$_2$ | 2-F | 4-F |
| —CH=CH$_2$ | 2-F | 4-Cl |
| —CH=CH$_2$ | 2-F | 4-Br |
| —CH=CH$_2$ | 2-F | 4-CF$_3$ |
| —CH=CH$_2$ | 2-Cl | H |
| —CH=CH$_2$ | 2-Cl | 4-F |
| —CH=CH$_2$ | 2-Cl | 4-Cl |
| —CH=CH$_2$ | 2-Cl | 4-Br |
| —CH=CH$_2$ | 2-Cl | 4-CF$_3$ |
| —CH=CH$_2$ | 2,4-diF | H |
| —CH=CH$_2$ | 2,4-diF | 4-F |
| —CH=CH$_2$ | 2,4-diF | 4-Cl |
| —CH=CH$_2$ | 2,4-diF | 4-Br |
| —CH=CH$_2$ | 2,4-diF | 4-CF$_3$ |
| —CH$_2$—CH=CH$_2$ | H | H |
| —CH$_2$—CH=CH$_2$ | H | 4-F |
| —CH$_2$—CH=CH$_2$ | H | 4-Cl |
| —CH$_2$—CH=CH$_2$ | H | 4-Br |
| —CH$_2$—CH=CH$_2$ | H | 4-CF$_3$ |
| —CH$_2$—CH=CH$_2$ | 2-F | H |
| —CH$_2$—CH=CH$_2$ | 2-F | 4-F |
| —CH$_2$—CH=CH$_2$ | 2-F | 4-Cl |

TABLE 2

| $R^1$ | X | Y |
|---|---|---|
| —CH$_2$—CH=CH$_2$ | 2-F | 4-Br |
| —CH$_2$—CH=CH$_2$ | 2-F | 4-CF$_3$ |
| —CH$_2$—CH=CH$_2$ | 2-Cl | H |
| —CH$_2$—CH=CH$_2$ | 2-Cl | 4-F |
| —CH$_2$—CH=CH$_2$ | 2-Cl | 4-Cl |
| —CH$_2$—CH=CH$_2$ | 2-Cl | 4-Br |
| —CH$_2$—CH=CH$_2$ | 2-Cl | 4-CF$_3$ |
| —CH$_2$—CH=CH$_2$ | 2,4-diF | H |
| —CH$_2$—CH=CH$_2$ | 2,4-diF | 4-F |
| —CH$_2$—CH=CH$_2$ | 2,4-diF | 4-Cl |

TABLE 2-continued

| R¹ | X | Y |
|---|---|---|
| —CH₂—CH=CH₂ | 2,4-diF | 4-Br |
| —CH₂—CH=CH₂ | 2,4-diF | 4-CF₃ |
| -Phenyl | H | H |
| -Phenyl | H | 4-F |
| -Phenyl | H | 4-Cl |
| -Phenyl | H | 4-Br |
| -Phenyl | H | 4-CF₃ |
| -Phenyl | 2-F | H |
| -Phenyl | 2-F | 4-F |
| -Phenyl | 2-F | 4-Cl |
| -Phenyl | 2-F | 4-Br |
| -Phenyl | 2-F | 4-CF₃ |
| -Phenyl | 2-Cl | H |
| -Phenyl | 2-Cl | 4-F |
| -Phenyl | 2-Cl | 4-Cl |
| -Phenyl | 2-Cl | 4-Br |
| -Phenyl | 2-Cl | 4-CF₃ |
| -Phenyl | 2,4-diF | H |
| -Phenyl | 2,4-diF | 4-F |
| -Phenyl | 2,4-diF | 4-Cl |
| -Phenyl | 2,4-diF | 4-Br |
| -Phenyl | 2,4-diF | 4-CF₃ |

Methods for preparing the compounds of the present invention are not particularly limited. For example, the compounds can be produced by similar methods to those of the triazole compounds described in the specification and claims of Japanese Patent Application No. 10-227939 such as 4-(4-chlorophenyl)-2-phenyl-3-(1,2,4-triazolyl)butan-2-ol. In the examples of the specification, the preparations of typical compounds of the present invention will be specifically explained in detail. Therefore, those skilled in the art can readily prepare the compounds of the general formula (I) by referring to the general descriptions given in the aforementioned specification, and specific explanations in the examples in the present specification, and appropriately choosing compounds as starting materials, reagents, reaction conditions and so forth, and by optionally adding suitable modifications and alterations to these methods. The reactive functional groups of compounds as starting materials or reagents may be protected with suitable protective groups, if necessary. Such protective groups can be appropriately chosen by those skilled in the art depending on the types of functional groups.

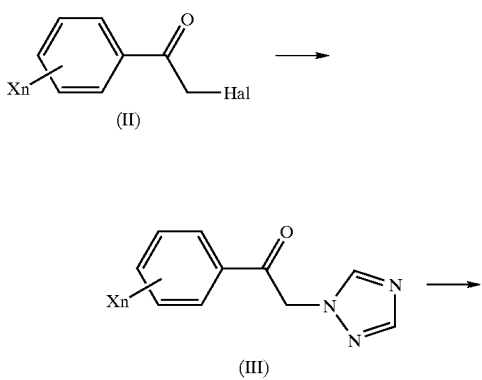

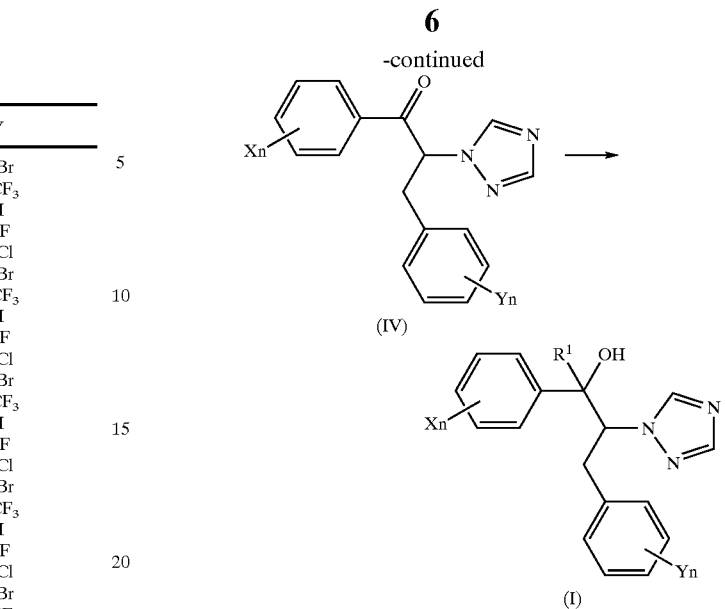

Compound (III) can be produced by reacting Compound (II) with 1,2,4-triazole or an alkali metal salt thereof in a suitable solvent such as acetone, acetonitrile, methanol, ethanol, and dimethylformamide in the presence of a suitable acid trapping agent such as potassium carbonate, sodium carbonate, potassium butoxide, sodium hydride, potassium hydride, sodium methoxide, and sodium ethoxide (in the scheme, Xn represents a hydrogen atom, or one or more substituents such as chlorine atom, fluorine atom, or methoxy group, and Hal represents chlorine atom, bromine atom, or iodine atom).

Compound (IV) can be prepared by reacting Compound (III) with a benzyl halide derivative in a suitable dry solvent such as methanol, ethanol, tetrahydrofuran, and dimethylformamide in the presence of a suitable base such as potassium butoxide, sodium hydride, potassium hydride, sodium methoxide, and sodium ethoxide (in the scheme, Yn represents one or more substituents such as chlorine atom, bromine atom, methyl group, trifluoromethyl group, or methoxy group).

Compound (I) of the present invention can be prepared by reacting an organometallic compound such as an allyl Grignard reagent or a phenyl Grignard reagent with Compound (IV) in an aprotic anhydrous solvent such as tetrahydrofuran, dimethylformamide, diglim, dioxane, and diethyl ether (in the scheme, R₁ has the same meaning as that defined in the formula (I), and Xn and Yn have the same meanings as those defined above).

The compounds of the present invention or salts thereof have specific inhibitory action against the brassinosteroid biosynthesis. Therefore, the compounds of the present invention or salts thereof are useful as, for example, active ingredients of plant growth regulators. The term "plant growth regulation" used in this specification should be construed in its broadest sense, including, for example, dwarfing of plants (suppression of plant elongation), pollen growth inhibition, retention of flower freshness, use of plant anti-stress agents (heat, dryness, coldness or the like), weed control by regulation of reproduction, suppression of plant retrogradation, control of hypertrophy of root and so forth. For example, plant growth dwarfing agents, plant growth retardants, herbicides and so forth are typical examples of the plant growth regulators of the present invention. However, the plant growth regulators of the present invention are not limited to these examples.

The plant growth regulators of the present invention can be formulated, for example, as an agricultural composition by using formulation additives well known in the art. Forms of the agricultural composition are not particularly limited, and any forms that can be used in the art may be chosen. For example, compositions in the forms of emulsions, liquids, oils, water soluble powders, wettable powders, flowables, powders, subtilized granules, granules, aerosols, fumigants, pastes and so forth can be used. The methods for manufacturing the agricultural composition are also not particularly limited, and any methods available to those skilled in the art can be appropriately employed. As the active ingredient of the plant growth regulators of the present invention, two or more of the compounds represented by the aforementioned formula (I) or salts thereof may be used in combination. Further, other active ingredients of agricultural chemicals such as insecticides, fungicides, insecticidal and fungicidal agents, herbicides and the like. Methods of application and doses of the plant growth regulators of the present invention can be suitably chosen by those skilled in the art depending on conditions including a purpose of application, a dosage form, a plot to be treated and so forth.

EXAMPLES

The present invention will be explained more specifically with reference to examples. However, the scope of the present invention is not limited to the following examples.

Example 1

Preparation of the Compound of the Present Invention (1) 2-(1,2,4-Triazolyl)acetophenone To 20 ml of dimethylformamide, 1.99 g of bromoacetophenone, 0.69 g of triazole, and 2 g of potassium carbonate were added, and the mixture was allowed to react at room temperature for 16 hours. The reaction mixture was poured into 100 ml of water, and the deposited crystals were collected by filtration, which were recrystallized from ethyl acetate/hexane to obtain the desired compound (yield: 85%).

(2) 2-(4-Chlorobenzyl)-2-(1,2,4-triazoyl)acetophenone

In 50 ml of dry dimethylformamide, 1.87 g of 2-(1,2,4-triazoyl)acetophenone was dissolved, and the solution was added with 0.48 g of 60% sodium hydride and stirred for 10 minutes with ice cooling. The reaction mixture was added dropwise with 1.61 g of 4-chlorobenzyl chloride dissolved in dimethylformamide. After completion of the dropwise addition, the reaction mixture was stirred for 2 hours, and then stopped by adding 1 ml of methanol. The solvent was evaporated under reduced pressure, and the residue was distributed between water and ether, and the ether layer was separated. The aqueous layer was further extracted twice with ether, and the ether layers were combined with the other ether layer, and then washed with saturated brine and dried over anhydrous magnesium sulfate. The solvent was evaporated under reduced pressure, and the residue was purified by silica gel column chromatography (hexane/ethyl acetate) to obtain the desired compound (yield: 68%).

6-(4-Chlorophenyl)-4-phenyl-5-(1,2,4-triazoyl)hexen-1-en-4-ol

The title compound was obtained by the following preparation method as a mixture of isomers in a ratio of 80:20.

Under a nitrogen flow, 0.312 g of 2-(4-chlorobenzyl)-2-(1,2,4-triazoyl)acetophenone was dissolved in 10 ml of dry tetrahydrofuran, and the solution was cooled to −80° C. with dry ice/acetone and stirred. The solution was added dropwise with 1.1 equivalents of a solution of allyl magnesium bromide in ether, and the reaction mixture was stirred for 30 minutes, and returned to room temperature. The reaction mixture was poured into an ammonium chloride solution, and extracted three times with ethyl acetate. The ethyl acetate layers were combined and washed with saturated brine, and dried over anhydrous magnesium sulfate, and then the solvent was evaporated under reduced pressure to obtain a residue. The residue was purified by silica gel column chromatography (hexane/ethyl acetate) to obtain the desired compound (total yield: 70%).

The desired product consisted of four stereoisomers, and each of the diastereomers was successfully separated by the above column chromatography into two fractions. The ratio of (A):(B) was 80:20, and each diastereomer was a mixture of equal amounts of enantiomers. Compound (A) was named as Brz2001 and Compound (B) as Brz2002.

$^1$H-NMR (300 MHz, CDCl$_3$)

Compound (A):

2.89 (d, 2H, J=7.6 Hz), 3.38 (dd, 1H, J=3.68, 14.0 Hz), 3.45 (dd, 1H, J=11.0, 14.0 Hz), 4.60 (dd, 1H, J=3.68, 14.0 Hz), 4.64 (s, 1H, OH), 5.13 (d, 1H, J=10.2 Hz), 5.20 (d 1H, J=17.1 Hz), 5.50–5.69 (m, 1H), 6.80 (d, 2H, J=8.1 Hz), 7.15 (d, 2H, J=8.1 Hz), 7.18–7.35 (m, 5H), 7.28 (s, 1H), 7.77 (s, 1H)

Compound (B):

1.94 (dd, 1H, J=7.60, 14.2 Hz), 2.54 (dd, 1H, J=6.60, 14.2 Hz), 2.72 (dd, 1H, J=2.72, 14.4 Hz), 3.21 (dd, 1H, J=11.72, 14.4 Hz), 4.15 (s, 1H, OH), 4.56 (dd, 1H, J=2.72, 11.72 Hz), 4.85 (d, 1H, J=17.1 Hz), 4.93 (d 1H, J=10.2 Hz), 5.30–5.42 (m, 1H), 6.59 (d, 2H, J=8.1 Hz), 7.10 (d, 2H, J=8.1 Hz), 7.34 (t, 1H, J=7.32 Hz), 7.45 (t, 1H, J=7.32 Hz), 7.53 (d, 2H, J=7.32), 7.80 (s, 1H), 8.06 (s, 1H)

Example 2

Inhibitory Action of the Compound of the Present Invention Against Biosynthesis of Brassinosteroid By using Brz2001 obtained in Example 1 and 4-(4-chlorophenyl)-2-phenyl-3-(1,2,4-triazolyl)butan-2-ol disclosed in the specification and claims of Japanese Patent Application No. 10-227939 (hereinafter referred to as "Brz91" in Example: this compound corresponds to Diastereomer (I) ("Compound 2") disclosed in Example 1 of said specification), inhibitory actions against elongation of the length of cress lower hypocotyl. Surfaces of cress seeds purchased were sterilized with 1% NaOCl solution for 20 minutes and washed 5 times with distilled water. The resulting cress seeds were sown on 1% agar-solidified medium (containing 0.5×Murashige and Skoog salts and 1.5% sucrose in Agripot (Kirin Brew Co., Tokyo)). The plants was grown in a growth chamber kept at 25□ under a cycle of 16 hour light (240 μEm-2s-1) and 8 hour dark conditions.

Figure 2:
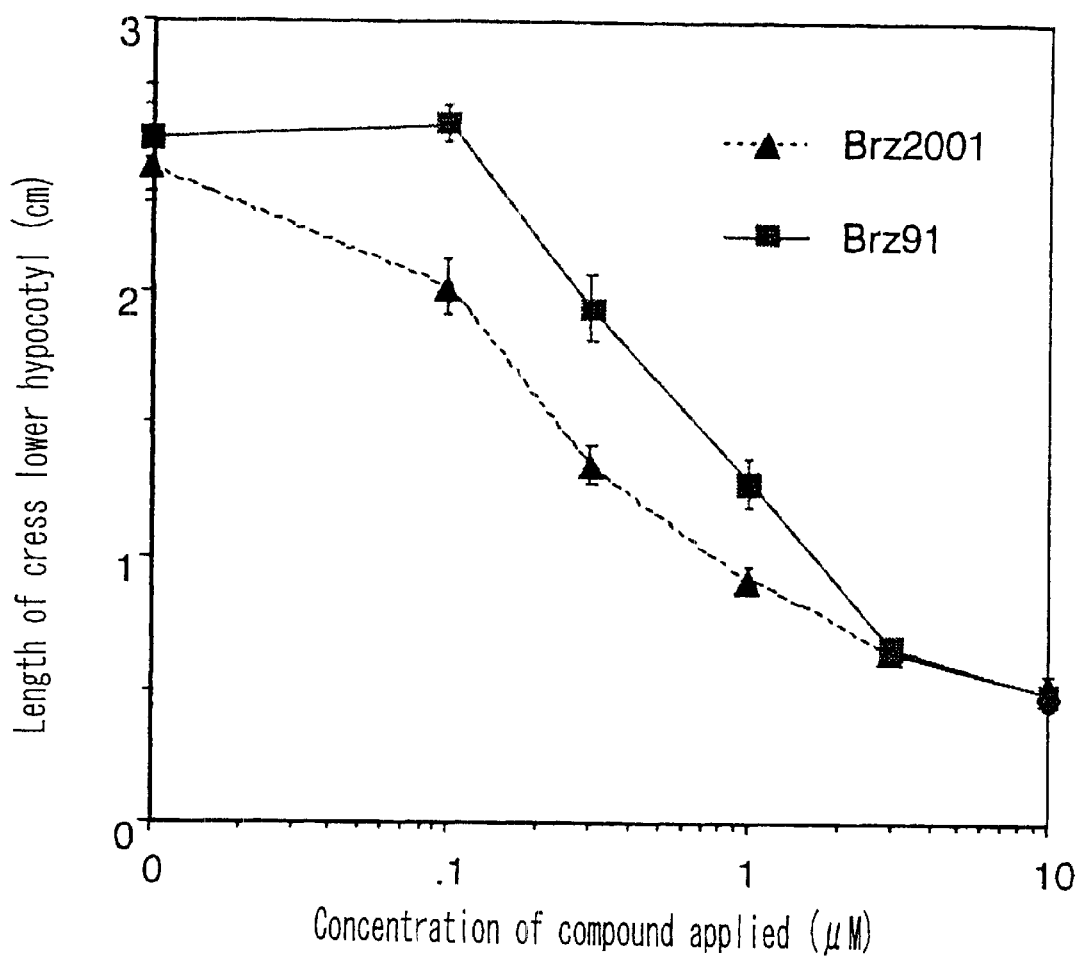
FIG. 2 shows inhibitory action of the compound of the present invention (Brz2000) against brassinosteroid biosynthesis with comparison of actions of Brz91.

Results are shown in FIGS. 1 and 2. Whether or not a tested drug is an inhibitor of brassinosteroid biosynthesis can be examined whether or not the inhibitory action is suppressed by addition of brassinolide which is considered as an active metabolite. The inhibitory effect of the compound of the present invention against elongation of cress lower hypocotyl was suppressed by addition of blassinolide, whilst not suppressed by addition of gibberellin (FIG. 1). From these results, it was verified that the compound of the present invention specifically inhibits brassinosteroid biosynthesis. In addition, it was found that the compound of the present invention had more potent inhibitory action against brassinosteroid biosynthesis than Brz91 (FIG. 2).

INDUSTRIAL APPLICABILITY

The compounds of the present invention have a specific inhibitory action against the brassinosteroid biosynthesis, and are useful as active ingredients of plant growth regulators and so forth.

What is claimed is:

1. A compound represented by the following formula (I):

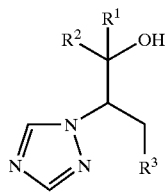

wherein $R^1$ represents a lower alkenyl group or a phenyl group which may be substituted, $R^2$ and $R^3$ independently represent a phenyl group which may be substituted, or a salt thereof.

2. The compound or a salt thereof according to claim 1, wherein $R^1$ is vinyl group, allyl group, butenyl group, or a phenyl group, $R^2$ is a phenyl which may be substituted, and $R^3$ is 4-chlorophenyl group.

3. 6-(4-Chlorophenyl)-4-phenyl-5-(1,2,4-triazolyl)hexen-1-en-4-ol or a salt thereof.

4. A plant growth regulator composition which comprises the compound according to claim 1 or a salt thereof as an active ingredient.

5. A method for regulating plant growth, which comprises administering the compound according to claim 1 or a salt thereof to a plant.

6. A plant growth regulator composition which comprises the compound according to claim 2 or a salt thereof as an active ingredient.

7. A plant growth regulator composition which comprises the compound according to claim 3 or a salt thereof as an active ingredient.

8. A method for regulating plant growth, which comprises administering the compound according to claim 2 or a salt thereof to a plant.

9. A method for regulating plant growth, which comprises administering the compound according to claim 3 or a salt thereof to a plant.

* * * * *